United States Patent
Sanz

[19]

[11] Patent Number: 5,873,374
[45] Date of Patent: Feb. 23, 1999

[54] CLEANING COMB WITH NEEDLES THAT ARE RUGGED ON THEIR PERIPHERAL SURFACE AND METHOD OF MANUFACTURING A HIGH MECHANICAL STRENGTH CLEANING COMB

[75] Inventor: Juan Martín Sanz, Buenos Aires, Argentina

[73] Assignee: Assistance S.R.L., Buenos, Argentina

[21] Appl. No.: 904,762

[22] Filed: Aug. 1, 1997

[51] Int. Cl.⁶ .................................................. A45D 24/30
[52] U.S. Cl. ........................... 132/125; 132/219; 132/163
[58] Field of Search .................................. 132/125, 219, 132/163, 159, 124; 119/625, 630, 632, 633

[56] References Cited

U.S. PATENT DOCUMENTS

| | | | |
|---|---|---|---|
| 2,270,528 | 1/1942 | Kirschenbaum | 132/125 |
| 2,546,541 | 3/1951 | Hunt | 132/149 |
| 2,605,773 | 8/1952 | Auclair | 132/137 |
| 4,612,945 | 9/1986 | Bachrach | 132/137 |
| 4,671,303 | 6/1987 | Saferstein | 132/149 |
| 5,318,051 | 6/1994 | Koppel | 132/126 |
| 5,353,817 | 10/1994 | Kantor et al. | 132/219 |
| 5,636,646 | 6/1997 | Zito | 132/149 |

*Primary Examiner*—Gene Mancene
*Assistant Examiner*—Pedro Philogene
*Attorney, Agent, or Firm*—Evenson, McKeown, Edwards & Lenahan, P.L.L.C.

[57] ABSTRACT

The present invention relates to a cleaning comb with needles that are rugged on their peripheral surface and a method of manufacturing a high mechanical strength cleaning comb. The comb includes a plurality of needles arranged parallel to each other with a spacing of under 100 μm, which are rugged on their peripheral surface for the purpose of more effectively removing foreign elements and smaller particles attached. The needles have a total length and a useful length, i.e. a relatively large portion that protrudes from the handle, and they have a diameter of over 1 mm. In order to give the comb a high mechanical strength, the method of assembling the comb includes attaching the needles onto the handle preferably by laser welding or soft soldering. The ruggedness on the peripheral surface is provided by cutting an helical groove or several parallel circumferential grooves.

55 Claims, 2 Drawing Sheets

CLEANING COMB WITH NEEDLES THAT ARE RUGGED ON THEIR PERIPHERAL SURFACE AND METHOD OF MANUFACTURING A HIGH MECHANICAL STRENGTH CLEANING COMB

FIELD OF THE INVENTION

The present invention relates to a cleaning comb with needles that are rugged on their peripheral surface and a method of manufacturing a high mechanical strength cleaning comb.

BACKGROUND OF THE INVENTION

While various types of combs that clear hair of strongly attached particles are known in the art, and particularly lice combs, the problem of foreign agents on human or animal hair has not yet been solved. The most important problem is that of nits (i.e. the eggs of human lice) for they are more strongly attached to hair.

In U.S. Pat. No. 4,612,945 there is described a comb that is useful to clear hair of lice and nits. This comb has teeth having a triangle-shaped cross section. The diameter of the teeth is tapered from the gripping ends to the leading ends, so that the distance between adjacent teeth is larger at the leading ends that close to the handle. The teeth are arranged with their longitudinal axes parallel to each other end on two different planes, with adjacent teeth staggered between both planes. With this design a scissors effect is achieved to detach lice and nits. This comb, however, has a few drawbacks. Its teeth have a limited length, whereby not always is it possible to reach the bottom of the hair. The distance between the leading ends of the teeth is substantially large, so the efficiency against lice and particularly against their eggs, is significantly reduced. In addition, teeth are triangle-shaped with sharp edges and thus they tend to damage hair, which is a totally undesired effect.

In U.S. Pat. No. 4,671,303 there is disclosed a nit comb and a method of manufacturing the same. The comb includes a plurality of metal teeth, which are mounted on a handle, with a distance between the teeth of about 100 $\mu$m to 120 $\mu$m. Each tooth is provided with an elongated groove that matches an elongated interconnection member in the handle, to insure the teeth are held parallel to each other both during manufacturing and in use. The teeth are of a convenient length, i.e. there is a portion of each tooth that protrudes from the handle and can be used to comb the hair, of approximately 9 mm, and the ends are hook-shaped to aid in removing lice and nits from de hair. In many instances the reduced effective length is not suitable for the comb to reach the base of the hair. Despite the particular shape of the tips of the teeth, the comb lacks the required efficiency to remove the particles that remain strongly attached to the hair, such as nits, because the distance between teeth is to big and the surface of the teeth is smooth, therefore leaving most of the eggs ungrasped.

SUMMARY OF THE INVENTION

It is an object of this invention to provide a comb with greatly improved characteristics to clean any type of hair or the like, of fastly attached particles, and particularly of objects such as nits which are generally firmly attached to the hair without damaging it at the same time.

It is another object of this invention to provide methods of manufacturing cleaning combs of high mechanical stress resistance, while still having needles of a relatively large useful length.

It is a further object to manufacture comb needles that have an uneven peripheral surface of accurately specified characteristics in order to remove particles that are strongly attached to the hair.

In a preferred embodiment, the cleaning comb with needles that have a rugged peripheral surface comprises parallel teeth arranged on a single plane with a spacing between teeth of under 100 $\mu$m, to effectively remove all the foreign elements and smaller particles attached to the hair.

To be effective, the needles must have a preferred useful length, i.e. the portion protruding from the handle, of at least 35 mm, since shorter teeth render the job of cleaning hair too burdensome, especially in the case of a full head of hair.

The needles are of a cross section without sharp edges, therefore, the cross section is circular or oval and they are preferably of a substantially cylindrical shape, so that do not damage or clutch the hair to be combed and cleaned.

The needles are made of a material that has a mechanical strength that is equal or greater than steel, and preferably of stainless steel with at least 1 mm diameter, to give the comb a higher mechanical strength in spite of their relatively large useful length, and which, on cleaning the hair, helps the comb overcome the resistance opposed by the nit.

The most important novel feature in the teeth is that they have a peripheral surface that is finely notched, which has the effect of removing foreign particles that are attached to the hair, to a significantly greater extent compared to the previous art teeth; for example, between 30 and 50% more nits can be removed using the cleaning comb of the present invention than the previous art combs.

While any uneven surface can be used to improve the cleaning effect of the comb, the preferred ruggedness, which offers the best cleaning and/or lowest manufacturing costs results are fine notches that are abrasive to the nit without damaging hair.

The notches may be provided as an helical slot with a pitch that is not too wide or as parallel ring-shaped circumferential slots with a specified limited spacing between them.

Preferably, the needles are attached to a handle that is made of sterilizable material, such as, for example, stainless steel, so that it can be boiled in tap water every day without undergoing any changes.

In a preferred embodiment, the method of assembling the cleaning comb comprises the steps of providing a plurality of needles which are of a relatively large total length; creating a ruggedness on the peripheral surface of each needle; honing and rounding up the distal tip of the leading end of each needleplacing the proximal ends of the needles side by side with a spacing between them that is less than 100 $\mu$m on the internal side of a first handle plate, so that they have a useful length, outside of the handle, of over 30 mm; arranging the needles slightly offset so that their leading ends make up a curved edge; firmly attaching the needles one by one onto said first handle plate, which gives the comb a high mechanical strength; and covering the handle with the second plate.

In a further preferred embodiment, the ruggedness is made by a method that comprises the steps of placing a cutting tool on a tool-holder device, with a spring to give it a constant pressure on the straightening roller train of a wire straightener-cutter; placing one of the plurality of needles inside the straightener; turning said straightening roller train together with said cutting tool around the needle, taking out cuttings in the shape of a groove; and, at the same time, advancing a needle through the straightening roller train, with the groove finally taking an helical shape on the peripheral surface of the needle; and repeating the above steps from the placing step on, for each of the plurality of needles.

In a further preferred embodiment a ruggedness is created using the steps of placing the needle inside a straightener; and cutting parallel circumferential grooves on the peripheral surface of the needle.

In order to provide a leading end that is more acceptable for the user, it is possible, during the placing step, to slightly offset the needles so that the leading ends of the comb form a curved edge.

In one of the preferred embodiments the needles are welded onto a first plate by laser welding. It is possible to apply the laser beam form the first plate side; or it may be applied from the needles side, but only between two adjacent needles so that the structure of the needles is not altered on applying the laser beam. In these embodiments the handle is seated by laser welding.of said second plate onto said first plate.

In a further preferred embodiment, the needles are soft soldered from the side of the needles. Here, the handle is press closed after an interposed plastic member has been inserted between the first plate and the second plate, which serves the purpose of aiding in the press closure.

BRIEF DESCRIPTION OF THE DRAWINGS

The above objects are achieved by the device of this invention, which is shown in the following figures, in which.

DETAILED DESCRIPTION OF THE INVENTION

Figure 1A:
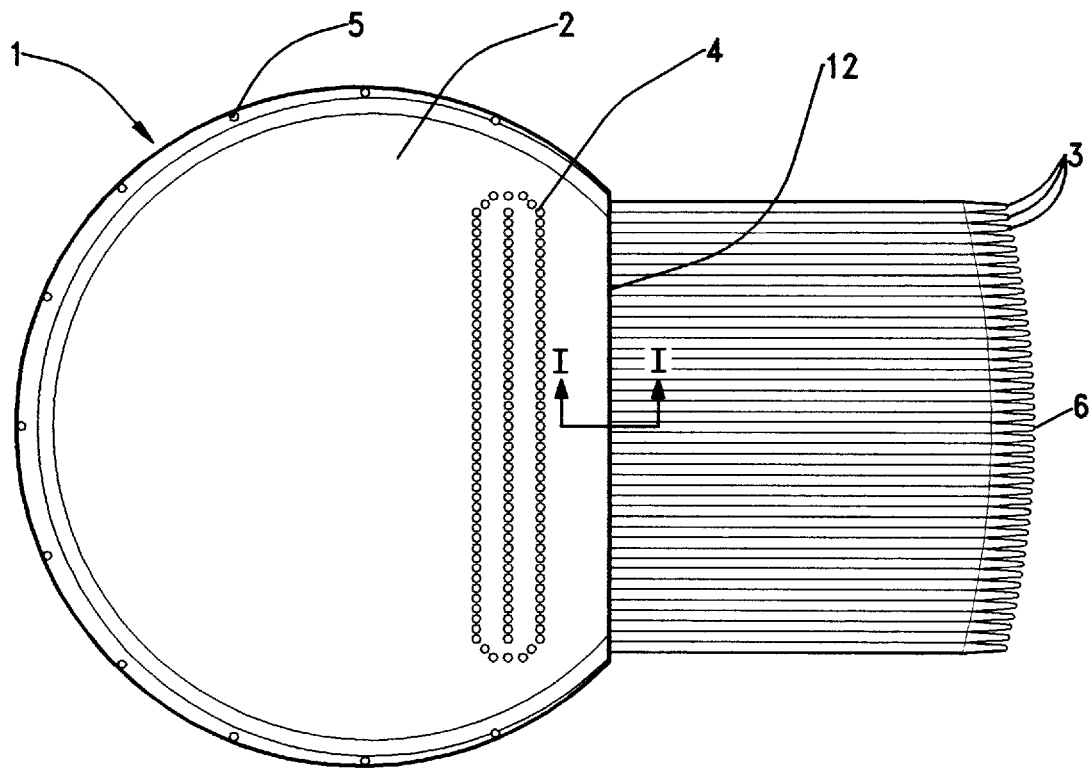
FIG. 1A is a top plane view of the first handle plate of the comb of the present invention.
Figure 1B:
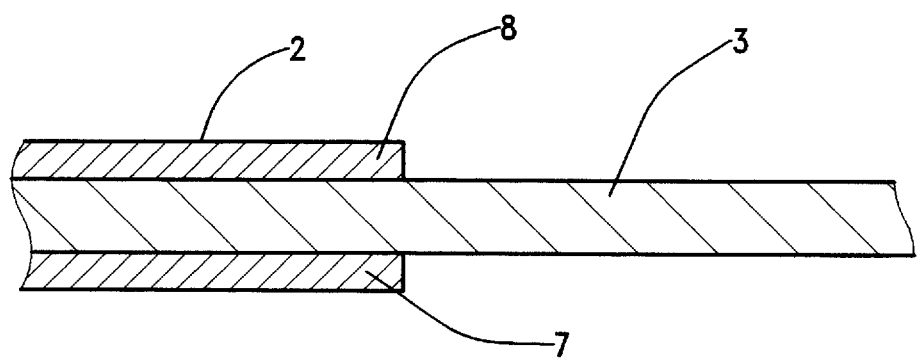
FIG. 1B is a partial section side view of the cleaning comb along the line I—I of FIG. 1A.

In FIG. 1A there is shown a comb 1 of the present invention, which comprises a plurality of needles 3, and two plates or covers, a first plate 7 and a second plate 8 (FIG. 1B), which make up the handle 2. The number of needles 3 may be from 10 to 100, and preferably the comb 1 comprises 33 individual needles or teeth 3.

The needles 3 consist of two portions. An active or useful portion ends, in its leading end, in a rounded conical extremity 11 (FIGS. 2A and 2D) and has a substantially cylindrical body with a peripheral surface machined either in the shape of an helix 9 (FIGS. 2A and 2C) or ring-shaped grooves 10 (FIGS. 2B). The remaining portion of the needles is the fastening portion that enters the handle 2 and is affixed to the first plate 7.

The needles 3 are made from cylindrical members with a diameter of 1,0 mm to 1,5 mm, and preferably of about 1,25 mm with a tolerance of about 0,01 mm, the needles being straight with a straightness tolerance of about 0,02 mm (FIGS. 2A and 2B), since needles of such diameter provide the comb with higher mechanical strengths which is required for the large useful length of the needles 3.

The needles have a ruggedness on their peripheral surface, which preferably consists of an helical groove 9 (FIG. 2A) or several parallel circumferential ring-shaped slots 10 (FIG. 2B).

In order to make a needle 3 a known wire straightener and cutter is used, to which is coupled, on one of its straightening roller trains, a cutting tool arranged on a tool-holder with a spring-to provide a constant pressure.

Said tool turns about the wire together with the straightening rollers, emitting turnings in the shape of a groove 9. Upon moving forward on the straightening roller train, groove 9 will finally take an helical shape 9 on the peripheral surface of the needle 3. The pitch of the helix 9 (FIG. 2A) is under 4 mm, and preferably under 2 mm.

So far, a straight cylindrical tube has been provided, which has an helically abraded surface. This tube-like member is taken to a sharpener, which is a centerless grinder that sharpens the tip in one or more cuts.

The scoring of the surface may also be achieved with this grinder, provided it is constructed with a suitable configuration; in this case the scoring consists of circumferences or circumferential grooves 10 that are parallel to each other with a spacing of 0,5 mm to 3 mm and preferably from 1 mm to 2 mm (FIG. 2B).

Figure 2A:
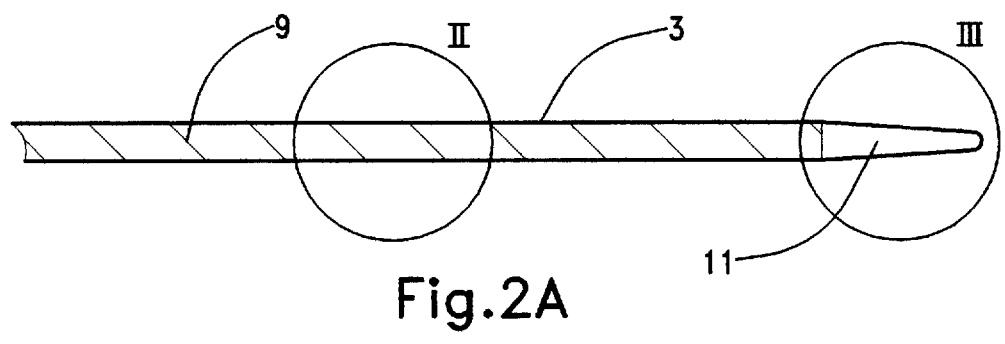
FIG. 2A is a side view of a tooth that has a ruggedness in the shape of an helical groove.
Figure 2B:
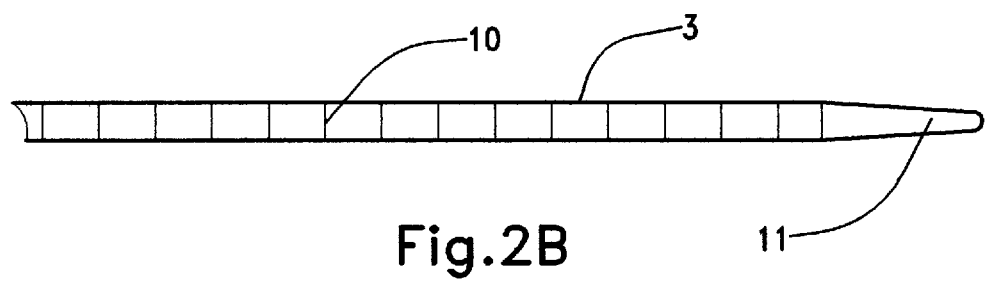
FIG. 2B is a side view of a tooth that has a ruggedness in the shape of parallel circunferential grooves.
Figure 2C:
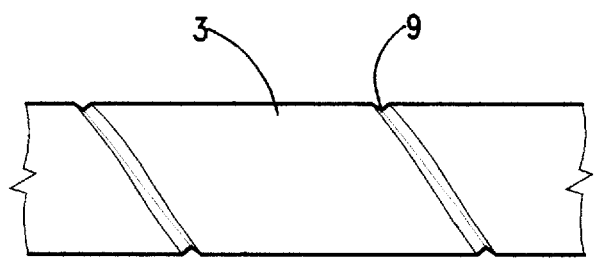
FIG. 2C is an enlarged view of part II of FIG. 2A.

As seen in FIG. 2C, both grooves 9 and grooves 10, have a greatly limited depth, of under 0,2 mm, and preferably under 0,1 to achieve its aim, the removal of foreign particles attached to the hair to be cleaned, such as lice and/or nits, without damaging hair.

Figure 2D:
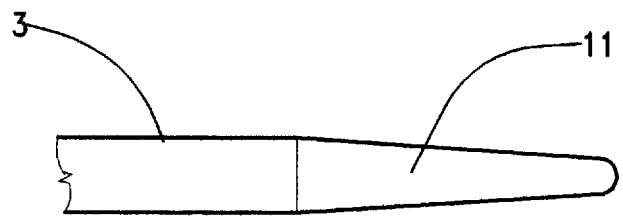
FIG. 2D is an enlarged view of part III of FIG. 2A.

Each needle, which has been provided with an helix 9 or with parallel circumferential grooves 10 on its peripheral surface, is then taken to a vibrating buffing machine which rounds up the conical leading end 11, as shown in FIGS. 2A and 2B. The length of the cone is between one and four times the diameter of the cylindrical member, and it is preferably three times the diameter of the cylindrical member. This cone ends in a 0,6 mm diameter hemisphere (FIG. 2D).

The needles prepared in such a way are arranged onto the first plate 7, parallel to each other, with a spacing between any two adjacent needles of between 50 μm and 100 μm, and preferably 90 μm. The needles are arranged so that a certain useful length of about 30 mm to 50 mm, and preferably of at least about 35 mm, starting from the right side 12 of the handle 2 is left outside the handle, for the purpose of combing and cleaning, and they have a total length of between 40 and 80 mm, and preferably of about 55 mm, to give the comb 1 a greater efficiency on any kind of hair to be cleaned with it.

When arranging the needles 3 on top of the first plate 7, they are slightly offset from the nearest needle, so that their leading ends altogether make up a curved edge 6 (FIG. 1A).

The fastening of the needles 3 onto the first plate 7 will be by individual soft soldering or laser welding and there will be at least 6 mm from the straight end 12 of the handle to the start of the welding.

Where needles 3 are laser welded onto the first plate 7, the laser beam may be applied either from the side of the first plate 7 or from the side of the needles 3.

When the first plate 7 is charged on first, it is firstly welded on two points of each needle 3 spaced at a distance of about 6 mm from each other and more than 6 mm away from the straight edge of the first plate 7, matching the respective axes of the needles 3, to keep them in place and to prevent them from being shifted, and thereafter a third point is welded on each needle 3 halfway between the previous ones.

When needles 3 are charged on first, they are welded with two or three laser points halfway between needles 3 at an equal distance from their axes, always at a distance of over 6 mm from the edge of the first plate 7.

After welding the needles 3 onto the first plate 7, there is placed the second plate 8 and the rounded edges of both plates 7, 8, are soldered with laser points 5 indistinctly, either from the side of the first plate 7 or from the side of the needles.

Where needles 3 are soft soldered, it is done first from the side of the needles 3. The handle is then closed pressing the second plate 8 on top of the first plate 7. In this case, an interposed member, that is not shown, is placed between both plates 7, 8 before pressing, so that it aids in the press fitting.

It is understood that the above detailed description is given only by way of illustration and that modifications and variations can be made without departing from the spirit and scope of the invention.

I claim:

1. A cleaning comb with needles that are rugged on their peripheral surface, which comprises a handle and a plurality of needles; wherein said comb is made of a sterilizable material having strength at least equal to steel; said handle comprising a first plate and a second plate; with each needle comprising a fastening end; a leading end and a peripheral surface; the fastening end of the needles being attached side by side to the inner surface of the first plate; the distance between any two adjacent needles being in the range of 50 $\mu$m to 100 8m; each needle having a total length in the range of 40 to 80 mm and a useful length, outside of the handle, that is in the range of 20 to 60 mm; the second plate being attached to the first plate and enclosing the fastening end of each needle; and said peripheral surface of each needle being provided with a ruggedness, and the leading end of each needle having a pointed and rounded tip.

2. The comb as claimed in claim 1, wherein the comb is made of steel.

3. The comb as claimed in claim 2, wherein each needle has a cylindrical shape with a diameter of at least 1 mm.

4. The comb as claimed in claim 3, wherein the distance between two adjacent needles is of about 90 $\mu$m.

5. The comb as claimed in claim 4, wherein each needle has a total length in the range of about 55 mm and a useful length, outside the handle, that is not less than 35 mm.

6. The comb as claimed in claim 5, wherein the plurality of needles comprises between 10 and 100 needles.

7. The comb as claimed in claim 6, wherein the plurality of needles comprises 33 needles.

8. The comb as claimed in claim 7, wherein the needles are offset from each other, the leading ends altogether forming a curved edge.

9. The comb as claimed in claim 8, wherein the ruggedness on the peripheral surface of each needle is a corresponding helical groove with a pitch of under 4 mm.

10. The comb as claimed in claim 9, wherein said helix has a pitch of under 2 mm.

11. The comb as claimed in claim 10, wherein the grooves are under 0,02 mm deep.

12. The comb as claimed in claim 11, wherein the grooves are under 0,01 mm deep.

13. The comb as claimed in claim 9, wherein the ruggedness on the peripheral surface of each needle consists of parallel circumferential grooves with a spacing of 0,5 to 3 mm from each other.

14. The comb as claimed in claim 13, wherein said parallel circumferential grooves are spaced at a distance of 1 to 2 mm from each other.

15. The comb as claimed in claim 14, wherein said parallel circumferential grooves are under 0,02 mm deep.

16. The comb as claimed in claim 15, wherein said parallel circumferential grooves are under 0,01 mm deep.

17. The comb as claimed in claim 16, wherein the comb further comprises a plastic interposed member disposed between the first plate and the second plate, which is capable of supporting the press fitting on press closing the handle.

18. A method of assembling a high mechanical strength cleaning comb, wherein said comb is made of a sterilizable material having a strength at least equal to steel; said method comprising the steps of providing a plurality of needles, which have a total length of 40 to 80 mm;

creating a ruggedness on the peripheral surface of each needle;

sharpening the distal tip of the leading end of each needle and rounding the end;

placing the proximal ends of the needles side by side at a distance of 50 $\mu$m to 100 $\mu$m from each other on the inner side or the first handle plate, so that the needles have a useful length, outside the handle, of 30 mm to 50 mm, arranging the needles slightly offset, with their leading ends forming a curved edge;

firmly attaching the needles one by one onto said first plate, thus giving the comb a high mechanical strength; and covering the handle with the second plate.

19. The method as claimed in claim 18, wherein the step of creating a ruggedness includes the steps of placing a cutting tool on a tool-holder, with a spring to provide a constant pressure, on a straightening roller train of a wire straightener-cutter;

placing one of the plurality of needles in the straightener;

turning said straightening roller train together with said cutting tool about the needle, emitting-turnings in the shape of a groove and, at the same time:

advancing the needle through the straightening roller train, the groove finally taking an helical shape on the peripheral surface of the needle; and repeating the above steps, from the placing step on, for each of the plurality of needles.

20. The method as claimed in claim 19, wherein the pitch of the helix is under 2 mm.

21. The method as claimed in claim 20, wherein the grooves are about 0,02 mm deep.

22. The method as claimed in claim 21, wherein the grooves are about 0,01 mm deep.

23. The method as claimed in claim 19, characterized by the step of creating a ruggedness including the steps of placing the needle inside a grinder and;

cutting circunferential parallel grooves on the peripheral surface of the needle.

24. The method as claimed in claim 23, characterized by the distance between grooves being from 0,5 to 3 mm.

25. The method as claimed in claim 24, wherein the grooves are under 0,02 mm deep.

26. The method as claimed in claim 25, wherein grooves are about 0,01 mm deep.

27. The method as claimed in claim 19, wherein the step of fastening is carried out by laser welding and the step of sealing the handle includes the step of laser welding said second plate onto said first plate.

28. The method as claimed in claim 27, wherein said laser welding is effected by applying the laser beam from the side of the first plate, including the steps of positioning each needle, applying the beam to each needle at that needle's respective place; and firmly attaching each needle by applying the beam to the area between said needle and the adjacent needle.

29. The method as claimed in claim 27, wherein said laser welding is effected by applying the laser beam from the side of the needles on the area between two adjacent needles.

30. The method as claimed in claim 18, wherein the step of attaching is carried out by soft soldering applied from the side of the needles; and the step of sealing the handle includes the steps of interposing plastic member between the first and the second plate, and pressing the second plate onto the first plate, said interposed plastic member supporting the press fitting.

31. A method of assembling a cleaning comb, wherein said comb is made of a sterilizable material having a strength at least equal to steel; said method comprising the steps of
   providing a plurality of needles, which have a total length of 40 to 80 mm and each having a forward end and a leading end with a distal tip,
   placing a cutting tool on a tool-holder, with a spring to give the cutting tool a constant pressure, on a straightening roller train of a wire cutter and straightener;
   placing one of the plurality of needles in the straightener;
   turning said straightening roller train together with said cutting tool around the needle, taking out turnings in the shape of a groove; and at the same time;
   advancing the needle through the straightening roller train, the groove finally taking the shape of a helix on the peripheral surface of the needle;
   sharpening the distal tip of the leading end of each needle and rounding the end;
   repeating the above stops, from the placing step on, for each of the plurality of needles;
   placing the fastening ends of the needles side by side spaced at a short distance from each other, on the inner side of the first plate of a handle, arranging the needles so that the needles are slightly offset, with their leading end forming a curved edge;
   attaching the needles one by one onto said first plate; and
   covering the handle with the second plate.

32. The method as claimed in claim 31, characterized by the pitch of the helix being under 2 mm.

33. The method as claimed in claim 32, wherein the grooves are under 0,02 mm deep.

34. The method as claimed in claim 33, characterized by the grooves being about 0,01 mm deep.

35. The method as claimed in claim 31, wherein the step of attaching is carried out by laser welding and the step of sealing the handle includes the step of laser welding said second plate onto said first plate.

36. The method as claimed in claim 35, wherein said laser welding is effected by applying the laser beam from the side of the first plate, including the steps of positioning each needle, applying the beam to each needle at that needle's respective place, and firmly attaching each needle by applying the beam to the area between said needle and the adjacent needle.

37. The method as claimed in claim 35, wherein said laser welding is effected by applying the laser beam from the side of the needles on the area between two adjacent needles.

38. The method as claimed in claim 31, wherein the step of attaching is carried out by soft soldering applied from the side of the needles; and the step of sealing the handle includes the steps of interposing a plastic member between the first and the second plate, and pressing the second plate onto the first plate, with said interposed plastic member supporting the press fitting.

39. A method of assembling a cleaning comb, wherein said comb is made of a sterilizable material having a strength at least equal to steel; said method comprising the steps of
   providing a plurality of needles, which have a total length of 40 to 80 mm and each having a forward end and a leading end with a distal tip;
   creating a ruggedness on the peripheral surface of each needle;
   sharpening the distal tip of the leading end of each needle and rounding;
   placing the proximal ends of the needles side by side at a distance of 50 µm to 100 µm from each other on the inner side of the first handle plate, so that the needles have a useful length, outside the handle, of 30 mm to 50 mm, arranging the needles slightly offset, with their leading ends forming a curved edge;
   laser welding the needles one by one onto said first plate; and
   laser welding said second place onto said first plate.

40. The method as claimed in claim 39, characterized by the step of creating a ruggedness including the steps of
   placing a cutting tool on a tool-holder, with a spring to provide a constant pressure, on a straightening roller train of a wire straightener-cutter;
   placing one of the plurality of needles in the straightener;
   turning said straightening roller train together with said cutting tool about the needle, taking out turnings in the shape of groove and, at the same time:
      advancing the needle through the straightening roller train, the groove finally taking an helical shape on the peripheral surface of the needle; and
   repeating the above steps, from the placing step on, for each of the plurality of needles.

41. The method as claimed in claim 40, wherein the pitch of the helix is under 2 mm.

42. The method as claimed in claim 41, wherein the grooves are about 0,02 mm deep.

43. The method as claimed in claim 42, wherein the grooves are about 0,01 mm deep.

44. The method as claimed in claim 39, characterized by the step of creating a ruggedness including the steps of
   placing the needle into a grinder; and
   cutting circumferential parallel grooves on the peripheral surface of the needle.

45. The method as claimed in claim 44, characterized by the distance between grooves being from 0,5 to 3 mm.

46. The method as claimed in claim 45, wherein the grooves are under 0,02 mm deep.

47. The method as claimed in claim 46, wherein the grooves are about 0,01 mm deep.

48. The method as claimed in claim 39, wherein said laser welding is effected by applying the laser beam from the side of the first plate, including the steps of positioning each needle applying the beam to each needle at its respective place; and firmly attaching each needle by applying the beam to the area between said needle and the adjacent needle.

49. The method as claimed in claim 39, wherein said laser welding is effected by applying the laser beam from the side of the needles to the area between two adjacent needles.

50. A method of assembling a cleaning comb, wherein said comb is made of a sterilizable material having a strength at least equal to steel, said method comprising the steps of providing a plurality of needles, which have a total length of 40 to 80 mm and each having a forward end and a leading end with a distal tip, placing a cutting tool on a tool-holder with a spring to give the tool a constant pressure, on a straightening roller train of a wire cutter-straightener;

placing one of the plurality of needles into the straightener;

turning said straightening roller train together with said cutting tool about the needle, taking out turnings in the shape of a groove; and at the same time;

advancing the needle through the straightening roller train, the groove finally taking the shape of a helix on the peripheral surface of the needle;

sharpening the distal tip of the leading end of each needle and rounding the end;

repeating the above steps, from the placing step on, for each of the plurality of needles;

placing the fastening ends of the needles side by side, spaced at a short distance from each other, on the inner side of the first plate of a handle, arranging the needles so that the needles are slightly offset, with their leading end forming a curved edge;

laser welding the needle one by one onto said first plate; and laser welding said second plate onto said first plate.

51. The method as claimed in claim 50, wherein the pitch of the helix is under 2 mm.

52. The method as claimed in claim 51, wherein the grooves are under 0,02 mm deep.

53. The method as claimed in claim 52, wherein the grooves are about 0,01 mm deep.

54. The method as claimed in claim 50, wherein said laser welding is effected by applying the laser beam from the side of the first plate, including the steps of positioning each needle, applying the beam to each needle at that needle's respective place, and firmly attaching each needle by applying the beam to the area between said needle and the adjacent needle.

55. The method as claimed in claim 50, wherein said laser welding is effected by applying the laser beam from the side of the needles to the area between two adjacent needles.

* * * * *